(12) United States Patent
Aoki

(10) Patent No.: US 6,967,191 B2
(45) Date of Patent: Nov. 22, 2005

(54) SYSTEM FOR TREATING EYE AND NERVE DISEASES IN DIABETIC AND NON-DIABETIC PATIENTS

(76) Inventor: Thomas T. Aoki, 1021 El Sur Way, Sacramento, CA (US) 95825

( * ) Notice: Subject to any disclaimer, the term of this patent is extended or adjusted under 35 U.S.C. 154(b) by 448 days.

(21) Appl. No.: 10/393,273

(22) Filed: Mar. 19, 2003

(65) Prior Publication Data

US 2003/0181357 A1 Sep. 25, 2003

Related U.S. Application Data

(62) Division of application No. 09/881,779, filed on Jun. 15, 2001, now Pat. No. 6,613,736.

(60) Provisional application No. 60/212,133, filed on Jun. 16, 2000.

(51) Int. Cl.$^7$ .............................................. A61K 37/26
(52) U.S. Cl. ............................................. 514/4; 514/3
(58) Field of Search ......................................... 514/4, 3

(56) References Cited

U.S. PATENT DOCUMENTS 4,826,810 A 5/1989 Aoki

OTHER PUBLICATIONS

Aoki, T. et al., "Chronic Intermittent Intravenous Insulin Therapy: A New Frontier in Diabetes Therapy", Diabetes Technology & Therapeutics, vol. 3, No. 1, 2001: 111-123.
Aoki, T. et al., "Long-term intermittent intravenous insulin therapy and type 1 diabetes mellitus", The Lancet, vol. 342, Aug. 28, 1993: 515-518.
Aoki Diabetes Research Institute, "CIIIT Treatment Results", Mar. 31, 2001.
Heinemann, L. et al., "Pulsatile insulin infusion and glucose homeostasis in well-controlled Type 1 (insulin-dependent) diabetic patients", J of Int Med, 1989, 226: 325-30.
Aoki, T. et al., "Effect of intensive insulin therapy on progression of overt nephropathy in Patients with type 1 diabetes mellitus", Endocrine Practice, vol. 5, No. 4, Jul./Aug. 1999; 174-178.

Primary Examiner—Bruce R. Campell
Assistant Examiner—Roy Teller
(74) Attorney, Agent, or Firm—Eric G. Masamori

(57) ABSTRACT

The present invention is a system capable of increasing retinal and neural glucose oxidation by enhancing pyruvate dehydrogenase activity and therefore treats retinopathy and central nervous system disorders in both diabetic and non-diabetic patients. The current invention is a system of the treating of eye and nerve diseases using insulin pulses to a patient utilizing Chronic Intermittent Intravenous Insulin Therapy to achieve an increase in retinal and neural glucose oxidation by enhancing pryuvate dehydrogenase activity, therefore treating retinopathy and central nervous system disorders in both diabetic and non-diabetic patients.

7 Claims, No Drawings

SYSTEM FOR TREATING EYE AND NERVE DISEASES IN DIABETIC AND NON-DIABETIC PATIENTS

CROSS REFERENCE TO OTHER APPLICATIONS

This application claims the benefit and is a division of U.S. patent application Ser. No. 09/881,779 filed on Jun. 15, 2001, now U.S. Pat. No. 6,613,736, which further claims the benefit of U.S. Provisional Patent Application No. 60/212,133 filed Jun. 16, 2000.

FIELD OF INVENTION

This invention relates to the treatment of eye and nerve diseases in diabetic and non-diabetic patients. More specifically, the invention relates to a system for treating eye and nerve diseases in diabetic and non-diabetic patients with Chronic Intermittent Intravenous Insulin Therapy.

BACKGROUND OF THE INVENTION

Diabetic retinopathy is a major cause of blindness in the United States. While earlier detection and major advances in laser therapies have made significant impact on this chronic complication of diabetes, the number of diabetic patients suffering from diabetic retinopathy continues to increase. The Diabetes Control and Complication Trial (DCCT) and the United Kingdom Prospective Diabetes Study (UKPDS) have both documented the benefit of tight blood glucose control on diabetic retinopathy and peripheral neuropathy. However, it is clear that tight blood glucose control was insufficient in 25% or more of the study participants to protect them from the onset or progression of diabetic retinopathy or neuropathy. It can be inferred that the number of patients who continued with tight control and nevertheless suffered from retinopathy and neuropathy would increase as time progressed. Indeed, during the first 1 to 1.5 years of studies designed to determine if tight blood glucose control would lessen diabetic complications, diabetic retinopathy actually increased dramatically in the tightly controlled patients. Other physicians have noted this increase in diabetic retinopathy in patients undergoing an acute and significant improvement in their blood glucose control. In the past, such worsening of diabetic retinopathy was attributed to decreased blood circulation in the retina and a consequent diminution in oxygen delivery to that tissue. However, such an explanation seemed less than credible in view of the short time course (1–1.5 years) and especially to the temporal relationship to the dramatic improvement in blood glucose control. This dichotomy suggested that the sudden worsening/appearance of diabetic retinopathy and other indications of neuropathy were linked to the fall in fasting, postprandial, and interprandial blood glucose levels.

What is needed is a system that increases retinal and neural glucose oxidation by enhancing pyruvate dehydrogenase activity and therefore treat retinopathy and central nervous system disorders in both diabetic and non-diabetic patients.

SUMMARY

Accordingly, the present invention is a system capable of increasing retinal and neural glucose oxidation by enhancing pyruvate dehydrogenase activity and therefore treats retinopathy and central nervous system disorders in both diabetic and non-diabetic patients. The current invention is the treating of eye and nerve diseases using insulin pulses to a patient utilizing Chronic Intermittent Intravenous Insulin Therapy to achieve an increase in retinal and neural glucose oxidation by enhancing pyruvate dehydrogenase activity, therefore treating retinopathy and central nervous system disorders in both diabetic and non-diabetic patients.

One preferred embodiment of the invention is a system for treating eye and nerve diseases in diabetic and non-diabetic patients through an intravenous administration of a pulse of insulin comprises a means for determining a respiratory quotient of a patient, a liquid or food containing glucose, an intravenous site, and a means of delivering a pulse of insulin at a regular interval of time.

In the preferred embodiment of the treatment system, any instrument capable of measuring the respiratory quotient determines a respiratory quotient of a patient. The respiratory quotient is defined as the ratio of carbon dioxide produced to oxygen consumed by the patient. In the preferred embodiment, a liquid or food containing glucose is consumed by the patient to prevent hypoglycemia. The preferred liquid or food containing glucose is GLUCOLA, however any similar liquid or food containing glucose that will prevent hypoglycemia in the patient may be used.

The preferred means of delivering insulin is an infusion device. It is preferable that the infusion device is capable of providing pulses of insulin on a prearranged interval, so long as there is sufficient glucose in the blood to keep the patient from becoming hypoglycemic. The preferred infusion device is also capable of delivering the pulses of insulin in as short duration of time as possible, without adversely affecting the vein at the site of infusion is used. However, less accurate devices may deliver the pulses and achieve the needed infusion profile.

In the preferred embodiment, the intravenous site is a temporary or permanent IV access site located in the body, forearm or hand of the patient. The amount of insulin is tailored to achieve increased retinal and neural glucose oxidation by enhanced pyruvate dehydrogenase activity. One method of monitoring retinal and neural glucose oxidation is PET scans. Alternatively, one may look for stabilization/reversal of diabetic retinopathy. In terms of neural function, there will be increased perception of sensation, especially in the feet, and a loss of the very painful "burning" or "pins and needles" sensation in the feet. There will also be improvement in autonomic neuropathy, especially gastroparesis and improvement in postural or orthostatic hypotension. Type 1 diabetic patients receive 20–35 milliunits of insulin per kilogram of body weight per pulse and type 2 diabetic patients receive 70–200 milliunits of insulin per kilogram of body weight per pulse. During periods of non-use, the IV site is preferably converted to a heparin or saline lock.

In one embodiment of the method of the invention, the patient is seated in a blood drawing chair and a 23 gauge needle/catheter is inserted into a body, hand or forearm vein to obtain vascular access. Although a 23 gauge needle catheter is preferred, any system of such access may accomplish the needed result, including indwelling catheters. After a short equilibration period, usually thirty minutes, the respiratory quotient (the ratio of carbon dioxide produced to oxygen consumed by the patient) of the patient is measured. The respiratory quotient measuring device may be any presently known model manufactured by any presently known supplier of such instruments. In the preferred embodiment, the patient is then asked to drink or eat liquid or food containing glucose usually on the order of 60 to 100 grams of glucose. In the preferred embodiment a pulse of insulin is administered intravenously on a regular interval of time, usually every six minutes, until the respiratory quotient (RQ) shows improvement, as indicated by a respiratory quotient of 0.90 or greater. In the preferred embodiment, improvement in RQ is generally achieved within one hour. In the preferred embodiment, the insulin/oral glucose phase is then followed by a rest period of usually one hour. In the preferred embodiment the entire procedure repeated until the desired effect is achieved.

The preferred method of insulin pulse delivery would be a prearranged interval, so long as there is sufficient glucose in the blood to keep the patient from becoming hypoglycemic. In order to determine the progress of the patient, it is preferable the RQ is measured every hour and blood glucose levels are checked every 30 minutes. The blood glucose level may be measured by any means which shows that the patient is not becoming hypoglycemic. In the preferred embodiment, the patient is free to move around after the initial insulin pulses have been administered. In the preferred embodiment, the intravenous site is converted to a heparin or saline lock. The patient dehydrogenase activity, therefore treating retinopathy and central nervous system disorders in both diabetic and non-diabetic patients.

The preferred embodiment of the invention is a system of delivering insulin pulses to a patient utilizing a Chronic Intermittent Intravenous Insulin Therapy. The preferred embodiment of the treatment system comprises a means for determining a respiratory quotient of a patient, a liquid or food containing glucose, an intravenous site, and a means of delivering a pulse of insulin at a regular interval of time.

The preferred means for determining a respiratory quotient of a patient is a SENSORMEDIC METABOLIC MEASUREMENT CART, however any instrument capable of measuring the respiratory quotient may be used. The respiratory quotient is defined as the ratio of carbon dioxide produced to oxygen consumed by the patient.

The liquid or food containing glucose is consumed by the patient to prevent the patient from becoming hypoglycemic. The preferred liquid or food containing glucose is GLUCOLA, but any similar type of liquid or food containing glucose may be given to the patient.

The preferred means of insulin delivery would be an infusion device capable of providing pulses of insulin on a prearranged interval, so long as there is sufficient glucose in the blood to keep the patient from becoming hypoglycemic. It is also preferable that the infusion device is capable of delivering the pulses of insulin in as short duration of time as possible, without adversely affecting the vein at the site of infusion is used. A BIONICA MD-110 infusion device is preferably used to administer the insulin pulses. However, less accurate devices may deliver the pulses and achieve the needed infusion profile.

In the preferred embodiment, the intravenous site is a temporary or permanent intravenous access site located in the body, forearm or hand of the patient, whereby insulin is provided by intravenous pulses in a highly accurate manner. A 23 gauge catheter is inserted into a hand or forearm vein in order to administer the insulin pulse, however any type of similar temporary or permanent intravenous access may be used. The amount of insulin is tailored to achieve increased retinal and neural glucose oxidation by enhanced pyruvate dehydrogenase activity. One method of monitoring retinal and neural glucose oxidation is PET scans. Alternatively, one can look for stabilization/reversal of diabetic retinopathy. In terms of neural function, there will be increased perception of sensation, especially in the feet, and a diminution or loss of the very painful "burning" or "pins and needles" sensation in the feet. There will also be improvement in autonomic neuropathy, especially gastroparesis and improvement in postural or orthostatic hypotension. Type 1 diabetic patients receive 20–35 milliunits of insulin per kilogram of body weight per pulse and type 2 diabetic patients receive 70–200 milliunits of insulin per kilogram of body weight per pulse. During periods of non-use, the intravenous site is preferably converted to a heparin or saline lock.

The preferred embodiment of the method of delivering insulin pulses to a patient utilizing Chronic Intermittent Intravenous Insulin Therapy is as follows. On the morning of the procedure, the patient is preferably seated in a blood drawing chair and a 23 gauge needle or catheter is preferably inserted into a hand or forearm vein to obtain vascular access. However, any system of such access may accomplish the needed result, including indwelling catheters, PICC lines, and PORTACATHs. After a short equilibration period the patient is asked to breathe into an instrument which measures the patient's respiratory quotient. Equilibrium is achieved when consecutive measurements of the respiratory quotient, at least 5 minutes apart, are the same and are less than 0.90. In practice the equilibration period is approximately thirty minutes, however any period of time that allows patient to establish a steady baseline, may be used. It is preferable that a SENSORMEDIC METABOLIC MEASUREMENT CART be used to measure the respiratory quotient, however, any presently known model manufactured by any presently known supplier of instruments capable of measuring a respiratory quotient may be used.

After the RQ is obtained, the patient is asked to consume a liquid or food containing glucose. The amount of glucose given to the patient ranged from 60 to 100 grams, however the amount of initial glucose given to the patient may vary. A pulse of insulin is then administered intravenously on a regular interval of time until the measured RQ shows improvement, as indicated by a RQ of 0.90 or greater. The usual interval of time was every six minutes, however, other regular intervals of time may be used. Improvement in RQ is generally achieved within one hour, however, the time required for RQ improvement may be shorter or longer than one hour.

The insulin/glucose phase is followed by a rest period of usually one hour. The rest period allows the elevated insulin levels to return to baseline. The entire procedure is repeated until the desired effect, RQ greater than 0.90, is achieved. The preferred method of insulin delivery would be providing pulses of insulin on a prearranged interval, so long as there is sufficient glucose in the blood to keep the patient from becoming hypoglycemic. In order to determine the progress of the patient, the RQ is measured every hour and blood glucose levels are checked every thirty minutes by any means which shows that the patient is not becoming hypoglycemic.

Once the insulin pulses have been administered and the patient shows RQ improvement as indicated by a RQ of 0.90 or greater, the patient is provided a rest period. During the rest period the patient is allowed to move around until the next series of insulin pulses are administered. During the rest period the IV site is preferably converted to a heparin or saline lock. The total time of the procedure is approximately 6–7 hours.

The amount of insulin is tailored to achieve increased retinal and neural glucose oxidation by enhanced pyruvate dehydrogenase activity. One method of monitoring retinal and neural glucose oxidation is PET scans. Alternatively, one may look for stabilization/reversal of diabetic retinopathy. In terms of neural function, there will be increased perception of sensation, especially in the feet, and a loss of the very painful "burning" or "pins and needles" sensation in the feet. There will also be improvement in autonomic neuropathy, especially gastroparesis and improvement in postural or orthostatic hypotension. Type 1 diabetic patients receive 20–35 milliunits of insulin per kilogram of body weight per pulse and type 2 diabetic patients receive 70–200 milliunits of insulin per kilogram of body weight per pulse.

Usually with a new patient two successive days of three treatments are performed the first week. For continuing patients the procedure is performed once a week. For patients who need/require a more intensive approach, the procedure may be repeated 3 or more times, including continuously, each week until the desired clinical outcome is achieved. The desired clinical outcome is the regression/stabilization of diabetic retinopathy, improvement in gastroparesis, improvement in postural hypotension, improvement in severe painful peripheral neuropathy and improved sensation in the feet. The intensive approach is designed for patients who are slow in achieving the aforementioned desired clinical outcomes.

In the non-diabetic patient more glucose may be required than in the diabetic patient, but the other parameters would remain the same, including the need for pulse delivery.

The following non-limiting example is given by way of illustration only.

EXAMPLE 1

Since mass action (e.g. high glucose concentrations) should facilitate glucose oxidation in the retina, it was conceived that the gradual lowering of the blood glucose level would result in diminished retinal glucose oxidation with the loss of the "mass action" effect due to the lowering of circulating blood glucose concentrations. It is also conceived that the diminished retinal glucose oxidation results in inadequate retinal energy stores. The key to this hypothesis is the relatively low activity of the pyruvate dehydrogenase complex in the retina of type 1 diabetic patients due to the low "free insulin" concentrations found in such patients whose only source of insulin is the subcutaneous injection of this hormone. The pyruvate dehydrogenase complex converts pyruvate to acetyl co-A.

Interim data indicates that this hypothesis is correct and the means to achieve a new treatment for retinopathy is suggested. Since insulin crosses the blood-brain barrier, intravenous insulin pulses, of 1–3 units will result in "free insulin" concentrations of 200–1000 microunits/ml in the vascular space and somewhat lower but still quite elevated insulin levels in the retina and other parts of the central and peripheral nervous system. The high concentrations of insulin reaching the retinal tissues and stimulating the exquisitely insulin sensitive pyruvate dehydrogenase complex and thereby facilitate retinal glucose oxidation and ensuring that the retina has adequate energy stores. As a consequence, diabetic and non-diabetic retinopathy due to similar processes will be stabilized (since the retina then be provided with newly adequate energy stores,) and in some cases, retinopathy reversed. Since the retina is part of the CNS, a similar improvement in both autonomic and peripheral nerves as well as the brain itself has also been observed in a number of both type 1 and 2 diabetic patients.

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A system for treating eye and nerve diseases associated with a diminution in glucose oxidation in patients through an intravenous site administering a pulse of insulin to a patient comprising:
   a) determining a respiratory quotient of the patient,
   b) having the patient consume a liquid or food containing glucose
   c) administering intravenously the pulse of insulin at a regular interval of time until the respiratory quotient is 0.90 or greater.

2. The system of claim 1, wherein the intravenous site further comprises a needle or catheter located in the patient's body, hand or forearm.

3. The system of claim 1, wherein the liquid or food contains 60 to 100 grams of glucose.

4. The system of claim 1, wherein the administered by the pulse of insulin is an intravenous infusion device.

5. The system of claim 1, wherein the interval of time is about six minutes.

6. The system of claim 1, wherein the pulse of insulin is tailored to achieve increased retinal and neural glucose oxidation by enhanced pyruvate dehydrogenase complex activity.

7. The system of claim 1, wherein the intravenous site is converted to a heparin or a saline lock during the rest period.

* * * * *